US012186066B2

(12) United States Patent
Peng et al.

(10) Patent No.: US 12,186,066 B2
(45) Date of Patent: Jan. 7, 2025

(54) NONCONTACT VITAL SIGN SENSING DEVICE

(71) Applicant: National Kaohsiung University of Science and Technology, Kaohsiung (TW)

(72) Inventors: Kang-Chun Peng, Kaohsiung (TW); Tzyy-Sheng Horng, Kaohsiung (TW); Fu-Kang Wang, Kaohsiung (TW); Meng-Che Sung, New Taipei (TW)

(73) Assignee: National Kaohsiung University of Science and Technology, Kaohsiung (TW)

( * ) Notice: Subject to any disclaimer, the term of this patent is extended or adjusted under 35 U.S.C. 154(b) by 366 days.

(21) Appl. No.: 17/742,551

(22) Filed: May 12, 2022

(65) Prior Publication Data

US 2023/0225626 A1 Jul. 20, 2023

(30) Foreign Application Priority Data

Jan. 20, 2022 (TW) .................................. 111102497

(51) Int. Cl.
*A61B 5/05* (2021.01)
(52) U.S. Cl.
CPC ....................................... *A61B 5/05* (2013.01)
(58) Field of Classification Search
CPC ..... A61B 5/0002; A61B 5/0015; A61B 5/002; A61B 5/0022; A61B 5/721; A61B 5/11; A61B 5/1113; A61B 5/05; A61B 8/08
See application file for complete search history.

(56) References Cited

U.S. PATENT DOCUMENTS

2018/0263502 A1* 9/2018 Lin .......................... G01S 7/415

FOREIGN PATENT DOCUMENTS

| TW | 201811262 A | 4/2018 | |
| TW | 202001278 A | 1/2020 | |
| WO | WO-2020146476 A1 * | 7/2020 | ........... A61B 5/0205 |

OTHER PUBLICATIONS

Kang-Chun Peng et al., Noncontact Vital Sign Sensing Under Nonperiodic Body Movement Using a Novel Frequency—Locked-Loop Radar, IEEE Transactions on Microwave Theory and Techniques, Aug. 2, 2021.
Kang-Chun Peng et al., Non-contact Vital Sign Detection Using Gain Detection Technique, 2021 IEEE International Symposium on Radio-Frequency Integration Technology (RFIT), Aug. 25-27, 2021.

* cited by examiner

*Primary Examiner* — Tammie K Marlen
(74) *Attorney, Agent, or Firm* — Demian K. Jackson; Jackson IPG PLLC

(57) ABSTRACT

In a noncontact vital sign sensing device of the present invention, a gain detector is provided to detect a gain between an oscillation signal and a received signal. Gain detection can cancel out the amplitude noise of an oscillator such that frequency information of vital sign(s) of a subject can be extracted from the gain without null-point issue, and vital sign(s) of the subject located at any position within sensing range can be detected.

10 Claims, 4 Drawing Sheets

NONCONTACT VITAL SIGN SENSING DEVICE

FIELD OF THE INVENTION

This invention generally relates to a vital sign sensing device, and more particularly to a noncontact vital sign sensing device.

BACKGROUND OF THE INVENTION

There are two types of conventional vital-sign sensor, contact type and noncontact type. The contact type vital-sign sensor has to contact subject's skin for a long time and be connected to electric wire, it causes the subject to feel uncomfortable and inconvenient, thus the noncontact type vital-sign sensor is current research focus. Doppler radar is the wide-used noncontact vital-sign sensor, Subject's body movement causes phase modulation on radar signals, and vital signs of the subject can be detected after phase demodulation of the radar signals. Single channel signals of the Doppler radar are usually phase-demodulated using a small angle approximation, but null detection point may be generated at the position of $4\pi/\lambda$. Although dual-baseband channel demodulation can solve the null-point problem, it may increase the complexity of the software and hardware.

SUMMARY

One object of the present invention is to detect a gain between an oscillation signal and a received signal using a gain detector, and the gain is provided for sensing vital sign(s) of a subject.

A noncontact vital sign sensing device includes an oscillator, a transmit antenna, a receive antenna, a gain detector and a data acquisition unit. The oscillator outputs an oscillation signal. The transmit antenna is coupled to the oscillator to receive the oscillation signal and transmits the oscillation signal to a subject as a transmitted signal, a reflected signal is reflected from the subject. The receive antenna receives the reflected signal as a received signal. The gain detector is coupled to the oscillator and the receive antenna to receive the oscillation signal and the received signal and detects a gain of the oscillation signal relative to the received signal. The data acquisition unit is electrically connected to the gain detector to receive the gain and outputs a vital sign of the subject according to the gain.

The gain detector of the present invention is provided to detect the gain between the oscillation signal and the received signal so as to prevent the amplitude noise of the oscillator from affecting vital sign detection. Furthermore, the vital sign of the subject can be extracted from the gain directly without the concern of null detection points.

DETAILED DESCRIPTION OF THE INVENTION

Figure 1:
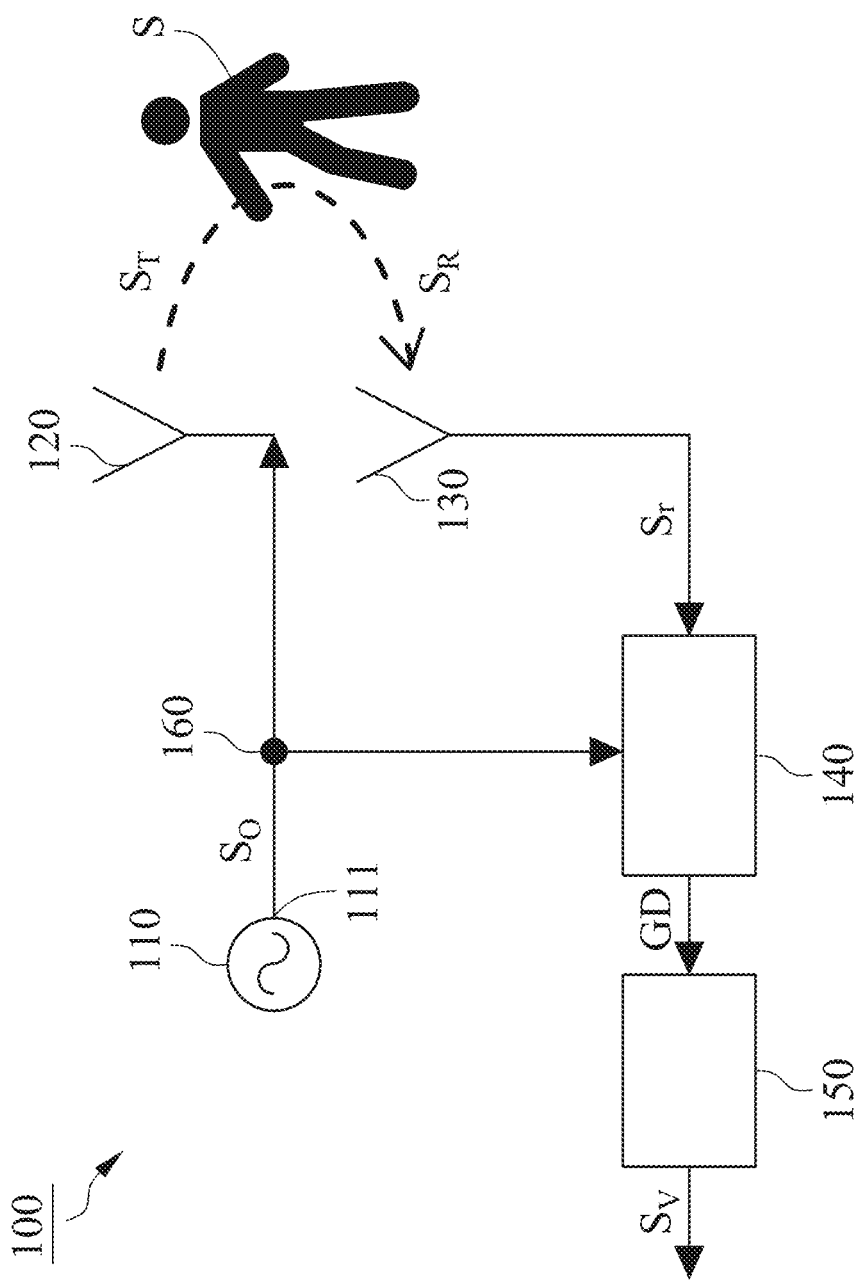
FIG. 1 is a block diagram illustrating a noncontact vital sign sensing device in accordance with a first embodiment of the present invention.

With reference to FIG. 1, a noncontact vital sign sensing device 100 in accordance with a first embodiment of the present invention includes an oscillator 110, a transmit (Tx) antenna 120, a receive (Rx) antenna 130, a gain detector 140, a data acquisition unit 150 and a first power splitter 160.

In this embodiment, the oscillator 110 is a voltage-controlled oscillator which receives a control voltage (not shown) to output an oscillation signal $S_o$ from an output port 111. The amplitude of the oscillation signal $S_o$ can be expressed as $$V_o(s) = V_{osc} + V_{n,osc}(s)$$

where $V_o(s)$ represents the Laplace transform of the amplitude of the oscillation signal $S_o$, $V_{osc}$ represents the amplitude of the oscillator 110, $V_{n,osc}(s)$ represents the Laplace transform of the amplitude noise of the oscillator 110. The first power splitter 160 is electrically connected to the oscillator 110 to receive the oscillation signal $S_o$ and is provided to split the oscillation signal $S_o$ into two parts. The Tx antenna 120 is electrically connected to the first power splitter 160 to receive one part of the oscillation signal $S_o$ and transmits the received oscillation signal $S_o$ to a subject as a transmitted signal $S_T$, and a reflected signal $S_R$ is reflected from the subject S.

The reflected signal $S_R$ is received by the Rx antenna 130 as a received signal $S_r$, and the amplitude of the received signal $S_r$ is expressed as $$V_{Rx}(s) = V_O(s)\frac{G_a}{R^2(s)} = [V_{osc} + V_{n,osc}(s)]\frac{G_a}{R^2(s)}$$

where $$G_a = \frac{G\lambda\sqrt{\sigma}F^2}{4\pi^{3/2}}$$

$$R(s) = L + x_b(s)$$

$V_{RX}(s)$ represents the Laplace transform of the amplitude of the received signal $S_r$, G is the gain of the Rx antenna 130, $\lambda$ is the wavelength of the received signal $S_r$, $\sigma$ is the radar cross section, F is the pattern propagation factor, L is the distance between the subject S and the noncontact vital sign sensing device 100, and $x_b(s)$ represents the Laplace transform of the vibration caused by vital sign(s) of the subject S.

The gain detector 140 is electrically connected to the first power splitter 160 and the Rx antenna 130 so as to receive the other part of the oscillation signal $S_o$ from the first power splitter 160 and receive the received signal $S_r$ from the Rx antenna 130. And the gain detector 140 is provided to detect a gain GD of the oscillation signal $S_o$ relative to the received signal $S_r$, the amplitude of the gain GD obtained by the gain detector 140 is expressed as $$V_{GD}(s) = K_{gd}\log\frac{V_O(s)}{V_{Rx}(s)} = 2K_{gd}\log R(s) - K_{gd}\log G_a$$

where $V_{GD}$ (s) represents the Laplace transform of the amplitude of the gain GD, $K_{gd}$ represents the sensitivity of the gain detector 140. It can be seen that $V_{n,osc}$ (the amplitude of the oscillator 110) is cancelled out to get R (s) and $G_\alpha$. Accordingly, $V_{n,osc}$ (the amplitude of the oscillator 110) is prevented from affecting the detection of vital sign(s), and vital sign(s) of the subject S can be obtained using the gain GD.

In this embodiment, the data acquisition unit 150 is electrically connected to the gain detector 140 to receive the gain GD and is provided to output a vital sign $S_v$ of the subject S according to the gain GD. The equation of the vital sign $S_v$ obtained by the data acquisition unit 150 is shown as $$V_{BB}(s) = 10^{\frac{V_{GD}(s)}{2K_{gd}}} = \frac{[L + x_b(s)]}{\sqrt{G_a}}$$

where $V_{BB}$ (s) represents the Laplace transform of the amplitude of the vital sign $S_v$. The vibration caused by vital sign of the subject S is the only variable, and after filtering the dc term of $V_{BB}(s)$, frequency information associated with heartbeat and respiration of the subject S can be extracted from signals for vital sign detection.

In this embodiment, the gain GD between the oscillation signal $S_o$ and the received signal $S_r$ detected by the gain detector 140 can be used to eliminate the amplitude noise of the oscillator 110 during vital sign sensing, and the vital sign $S_v$ of the subject S can be extracted from the gain GD without null-point issue. Consequently, the vital sign $S_v$ of the subject S located at any distance from the noncontact vital sign sensing device 100 can be detected.

Figure 2:
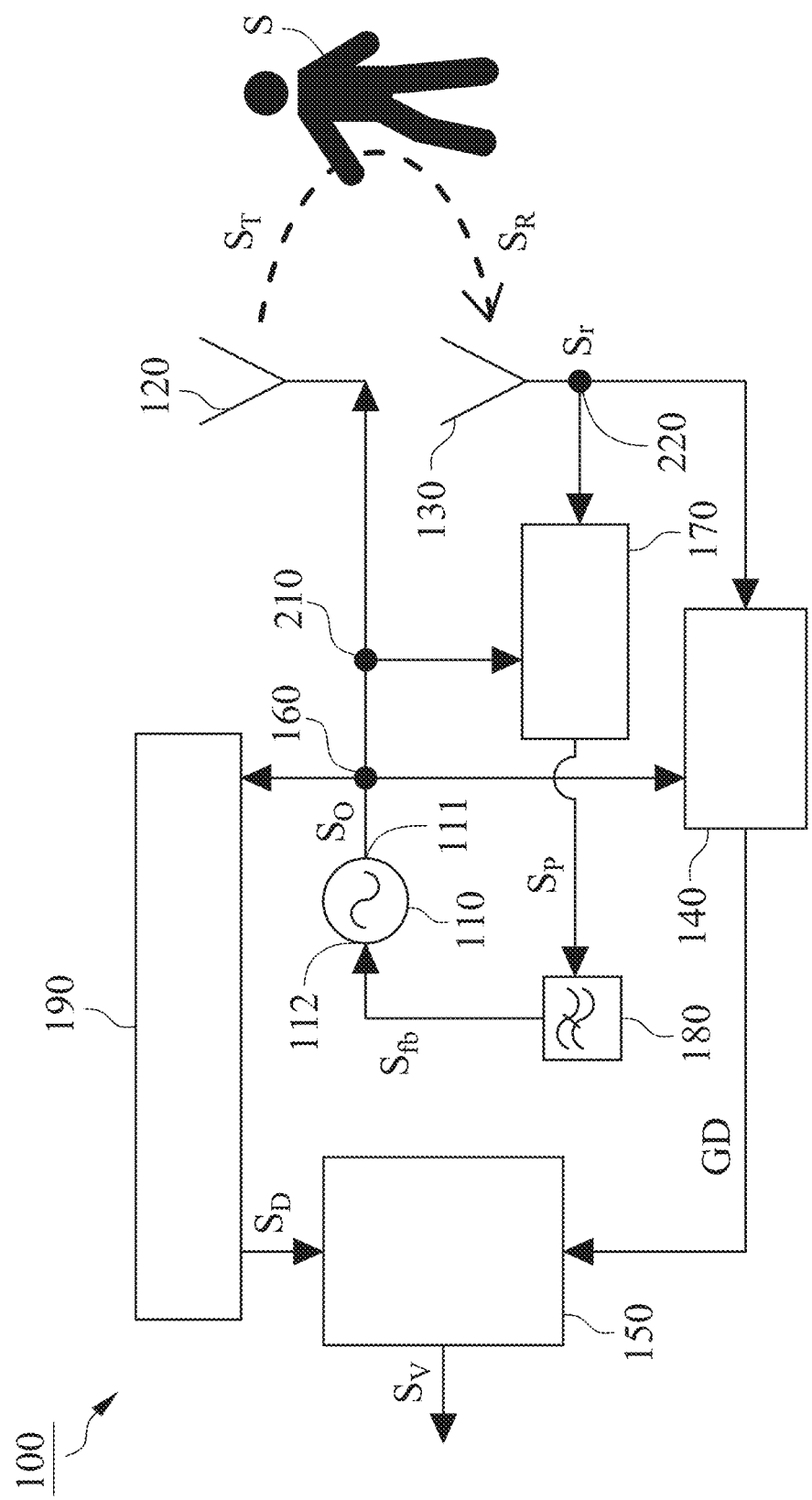
FIG. 2 is a block diagram illustrating a noncontact vital sign sensing device in accordance with a second embodiment of the present invention.

FIG. 2 is a circuit diagram showing a noncontact vital sign sensing device 100 of a second embodiment of the present invention. Compared with the first embodiment, the noncontact vital sign sensing device 100 of the second embodiment further includes a phase detector 170, a loop filter 180, a demodulator 190, a second power splitter 210 and a third power splitter 220. In the second embodiment, the oscillation signal $S_o$ is received and divided into three parts by the first power splitter 160 and delivered to the gain detector 140, the demodulator 190 and the second power splitter 210, respectively. One part of the oscillation signal $S_o$ received by the second power splitter 210 is split into two parts and delivered to the Tx antenna 120 and the phase detector 170, respectively. The third power splitter 220 electrically connected to the Rx antenna 130 receives and split the received signal $S_r$ into two parts. Two parts of the received signal $S_r$ are delivered to the phase detector 170 and the gain detector 140, respectively.

The phase detector 170 receives the oscillation signal $S_o$ and the received signal $S_r$ from the second power splitter 210 and the third power splitter 220 and detects a phase difference between the oscillation signal $S_o$ and the received signal $S_r$ to output a phase detection signal Sp. The loop filter 180, which is electrically connected to the phase detector 170, receives and filter the phase detection signal Sp to output a feedback signal $S_{fb}$ to a tuning port 112 of the oscillator 110. The demodulator 190 receives the oscillation signal $S_o$ from the first power splitter 160 and outputs a demodulated signal $S_D$ to the data acquisition unit 150. And the data acquisition unit 150 outputs the vital sign $S_v$ according to the gain GD and the demodulated signal $S_D$.

As the subject S has body movement(s) with respect to the Tx antenna 120, e.g. chest displacement as a result of respiration and heartbeat, the relative motion between the subject S and the Tx antenna 120 may induce the Doppler effect on the transmitted signal $S_T$ so as to lead the reflected signal $S_R$ and the received signal $S_r$ contain the Doppler phase shift caused by the movement of the subject S. After filtering high-frequency component in the phase detection signal Sp output from the phase detector 170 by the loop filter 180, the feedback signal $S_{fb}$ containing low-frequency component is the Doppler phase shift caused by the relative motion between the subject S and the Tx antenna 120. The feedback signal $S_{fb}$ is fed back into the tuning port 112 of the oscillator 110 to cause frequency shift of the oscillator 110, accordingly, the body movement of the subject S can be detected by measurement of the frequency shift of the oscillator 110. Moreover, due to the oscillator 110 has high tuning sensitivity, the vital sign $S_v$ of the subject S located at any position within the sensing range can be detected by phase detection using the phase detector 170 without null-point issues.

In the second embodiment, the oscillator 110, the Tx antenna 120, the time delay from the Tx antenna 120 to the subject S, the time delay from the subject S to the Rx antenna 130, the phase detector 170 and the loop filter 180 compose a wireless frequency-locked loop, accordingly, the body movement of the subject S can be detected using the frequency shift of the oscillator 110. Moreover, the delay of the delay unit in the wireless frequency-locked loop is positively correlative to phase noise suppression so the time delay from the Tx antenna 120 to the subject S and the time delay from the subject S to the Rx antenna 130 in this embodiment are used as the delay unit of the wireless frequency-locked loop, and the phase noise suppression is greater as the subject S is farther away from the noncontact vital sign sensing device 100. The sensitivity of the noncontact vital sign sensing device 100 corresponding to the body movement of the subject S will not be decreased obviously even if the distance between the subject S and the noncontact vital signs sensing device 100 is increased.

Figure 3:
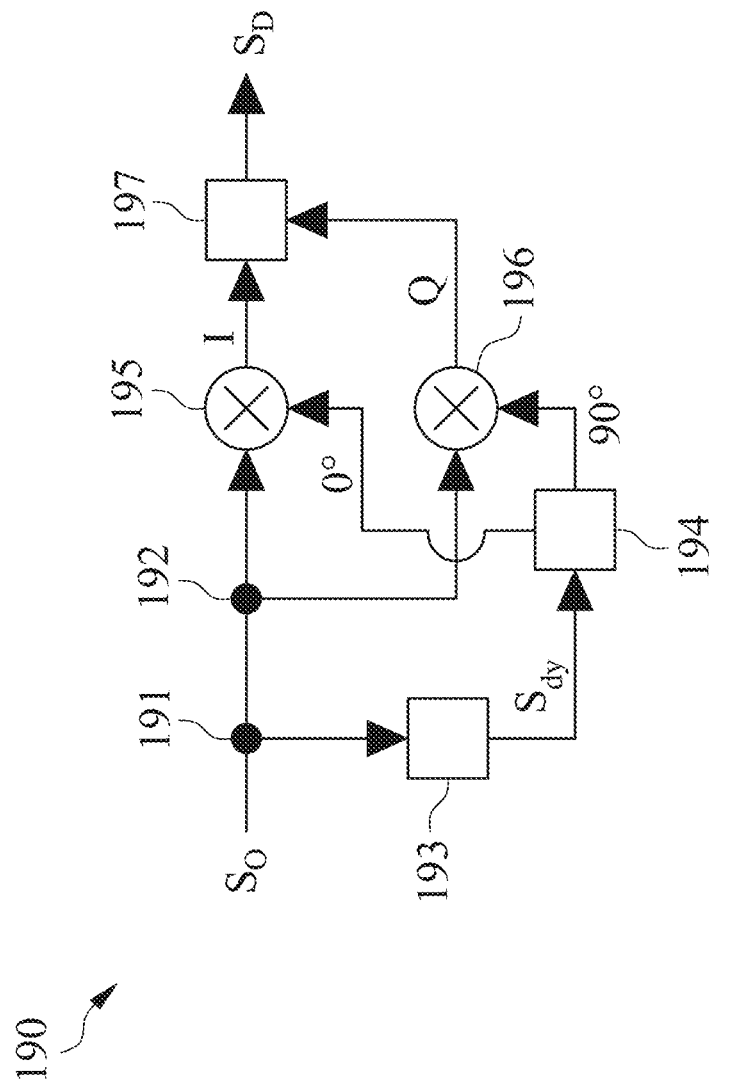
FIG. 3 is a circuit diagram illustrating a demodulator of the noncontact vital sign sensing device in accordance with the second embodiment of the present invention.

With reference to FIGS. 2 and 3, the demodulator 190 is provided to frequency-modulate the oscillation signal $S_o$ to obtain the vital sign $S_v$ of the subject S. In the second embodiment, the demodulator 190 includes a fourth power splitter 191, a fifth power splitter 192, a delay unit 193, a quadrature power splitter 192, a first mixer 195, a second mixer 196 and an arctangent demodulation unit 197. The fourth power splitter 191 is electrically connected to the first power splitter 160 to receive and split the oscillation signal $S_o$ into two parts. The delay unit 193 is electrically connected to the fourth power splitter 191 to receive one part of the oscillation signal $S_o$ and thus outputs a delayed signal $S_{dy}$. The quadrature power splitter 194 is electrically connected to the delay unit 193 to receive the delayed signal $S_{dy}$ and is provided to output an in-phase signal 0° and a quadrature signal 90°. The fifth power splitter 192 is electrically connected to the fourth power splitter 191 to receive the other part of the oscillation signal $S_o$ and is provided to split the received oscillation signal $S_o$ into two parts. The first mixer 195 is electrically connected to the fifth power splitter 192 and the quadrature power splitter 194 to receive one part of the oscillation signal $S_o$ and the in-phase signal 0° and thus output an in-phase mixed signal I. The second mixer 196 is electrically connected to the fifth power splitter 192 and the quadrature power splitter 194 to receive the other part of the oscillation signal $S_o$ and the quadrature signal 90° and output a quadrature mixed signal Q. The arctangent demodulation unit 197 is electrically connected to the first mixer 195 and the second mixer 196 to receive the in-phase mixed signal I and the quadrature mixed signal Q, and quadrature-demodulates the in-phase signal I and the quadrature mixed signal Q to output the demodulated signal $S_D$, which involves the frequency information of the vital sign $S_v$ of the subject S, to the data acquisition unit 150.

With reference to FIG. 2, both of the gain GD and the demodulated signal $S_D$ involve the frequency information of the vital sign $S_v$ of the subject S, accordingly, after receiving the gain GD and the demodulated signal $S_D$, the data acquisition unit 150 superposes the gain GD and the demodulated signal $S_D$ into the vital sign $S_v$. Consequently, the strength of the vital sign $S_v$ and the noise suppression can be enhanced to enhance the signal-to-noise ratio of the vital sign $S_v$.

Preferably, for better signal-to-noise ratio, the data acquisition unit 150 superposes the gain GD and the demodulated signal $S_D$ into the vital sign $S_v$ by applying a cross correlation function (CCF) which is shown as $$S_{\phi v}(s) = S_{\phi,BB}(s) S_{V,BB}(s)$$

where $S_{\phi v}(s)$ represents the Laplace transform of the power spectrum density (PSD) of the vital sign $S_v$ obtained by applying a CCF, $S_{\phi,BB}(s)$ represents the Laplace transform of PSD of the demodulated signal $S_D$, and $S_{v,BB}(s)$ represents PSD of $V_{BB}(s)$ after filtering dc term.

Figure 4:
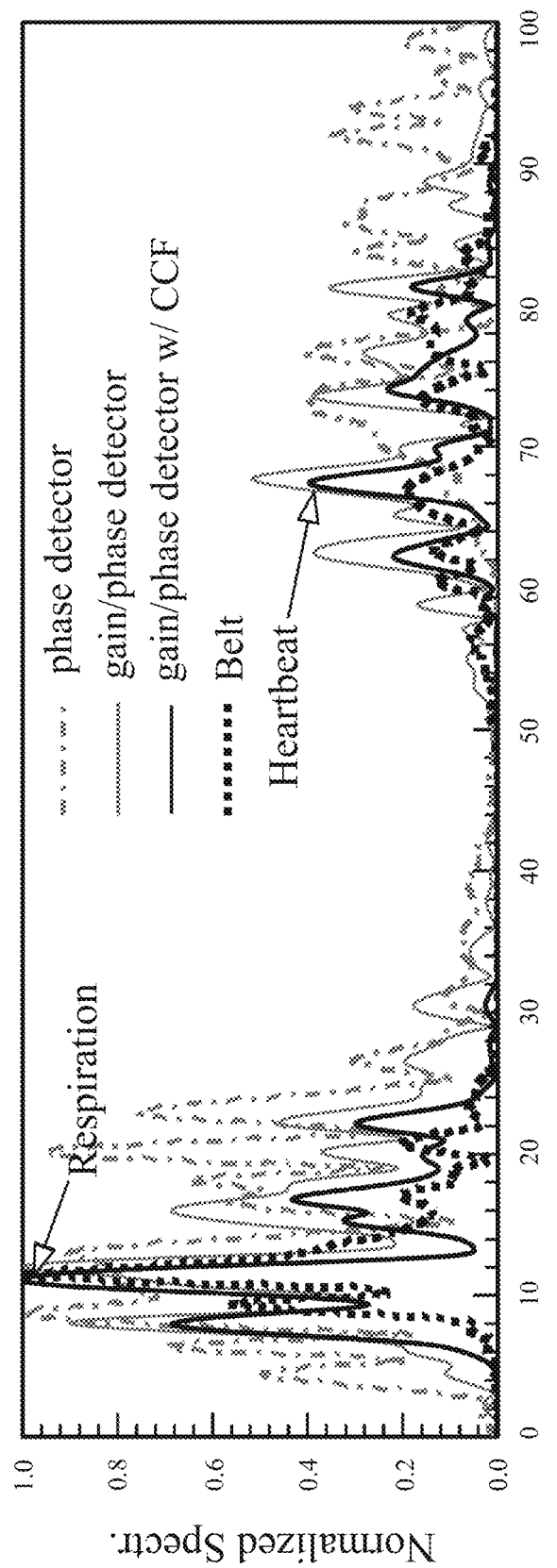
FIG. 4 is spectra measured using the noncontact vital sign sensing device in accordance with the second embodiment of the present invention and a conventional vital-sign sensor.

Spectra measured using the noncontact vital sign sensing device 100 of the second embodiment of the present invention and a conventional vital-sign sensor (Vernier GDX-RB chest belt) is shown in FIG. 4, the subject S was located at a distance of 1.5 m away and talked with others. Speaking caused vibrations in the chest thus remarkable harmonics can be found in the spectrum measured using the wireless frequency-locked loop with phase detector only, by contrast, regardless of the cross correlation function (CCF), there are less harmonics of vital signs in the spectrum obtained by mixing the signals detected by the gain detector 140 and the phase detector 170. The noncontact vital sign sensing device 100 including the gain detector 140 and the phase detector 170 can provide better signal-to-noise ratio of vital sign caused by weak heartbeat than the conventional vital-sign sensor, the noncontact vital sign sensing device 100 has excellent sensitivity for vital sign detection.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A noncontact vital sign sensing device comprising:
an oscillator configured to output an oscillation signal;
a transmit antenna coupled to the oscillator and configured to receive and transmit the oscillation signal to a subject as a transmitted signal, a reflected signal is configured to be reflected from the subject;
a receive antenna configured to receive the reflected signal as a received signal;
a gain detector coupled to the oscillator and the receive antenna and configured to receive the oscillation signal and the received signal and configured to detect a gain of the oscillation signal relative to the received signal; and
a data acquisition unit electrically connected to the gain detector and configured to receive the gain and output a vital sign of the subject according to the gain, wherein the gain is represented by an equation as follows:

$$V_{GD}(s) = K_{gd} \log \frac{V_{Tx}(s)}{V_{Rx}(s)}$$

where $V_{GD}(s)$ represents an amplitude of the gain, $K_{gd}$ represents a sensitivity of the gain detector, $V_{Tx}(s)$ represents an amplitude of the oscillation signal, and $V_{Rx}(s)$ represents an amplitude of the received signal.

2. The noncontact vital sign sensing device in accordance with claim 1, wherein the vital sign obtained by the data acquisition unit is represented by an equation as follows:

$$V_{BB}(s) = 10^{\frac{V_{GD}(s)}{2K_{gd}}}$$

where $V_{BB}(s)$ represents an amplitude of the vital sign.

3. The noncontact vital sign sensing device in accordance with claim 1 further comprising a first power splitter, wherein the first power splitter is electrically connected to the oscillator and configured to receive and split the oscillation signal into two parts, one part of the oscillation signal is configured to be delivered to the transmit antenna and the other part of the oscillation signal is configured to be delivered to the gain detector.

4. The noncontact vital sign sensing device in accordance with claim 1 further comprising a phase detector, a loop filter and a demodulator, wherein the phase detector is coupled to the oscillator and the receive antenna and configured to detect a phase difference between the oscillation signal and the received signal and output a phase detection signal, the loop filter is electrically connected to the phase detector and configured to receive the phase detection signal and output a feedback signal to a tuning port of the oscillator, the demodulator is coupled to the oscillator and configured to receive the oscillation signal and output a demodulated signal to the data acquisition unit, the data acquisition unit is configured to output the vital sign according the gain and the demodulated signal.

5. The noncontact vital sign sensing device in accordance with claim 4 further comprising a first power splitter, a second power splitter and a third power splitter, wherein the first power splitter is electrically connected to the oscillator and configured to receive and split the oscillation signal into three parts, the gain detector, the second power splitter and the demodulator are electrically connected to the first power splitter and configured to receive three parts of the oscillation signal, respectively, the second power splitter is configured to split the received oscillation signal into two parts, the transmit antenna and the phase detector are electrically connected to the second power splitter and configured to receive two parts of the oscillation signal, respectively, the third power splitter is electrically connected to the receive antenna and configured to receive and split the received signal into two parts, the phase detector and the gain detector are electrically connected to the third power splitter and configured to receive two parts of the received signal, respectively.

6. The noncontact vital sign sensing device in accordance with claim 5, wherein the demodulator includes a fourth power splitter, a fifth power splitter, a delay unit, a quadrature power splitter, a first mixer, a second mixer and an arctangent demodulation unit, the fourth power splitter is electrically connected to the first power splitter and configured to receive and split the oscillation signal into two parts, the delay unit is coupled to the oscillator and configured to receive the oscillation signal and output a delayed signal, the quadrature power splitter is electrically connected to the delay unit and configured to receive the delayed signal and output an in-phase signal and a quadrature signal, the first mixer is coupled to the oscillator and the quadrature power splitter and configured to receive the oscillation signal and the in-phase signal and output an in-phase mixed signal, the second mixer is coupled to the oscillator and the quadrature power splitter and configured to receive the oscillation signal and the quadrature signal and output a quadrature mixed signal, the arctangent demodulation unit is electrically connected to the first mixer and the second mixer and configured to receive the in-phase mixed signal and the quadrature mixed signal and output the demodulated signal to the data acquisition unit.

7. The noncontact vital sign sensing device in accordance with claim 4, wherein the demodulator includes a delay unit, a quadrature power splitter, a first mixer, a second mixer and an arctangent demodulation unit, the delay unit is coupled to the oscillator and configured to receive the oscillation signal and output a delayed signal, the quadrature power splitter is electrically connected to the delay unit and configured to receive the delayed signal and output an in-phase signal and a quadrature signal, the first mixer is coupled to the oscillator and the quadrature power splitter and configured to receive the oscillation signal and the in-phase signal and output an in-phase mixed signal, the second mixer is coupled to the oscillator and the quadrature power splitter and configured to receive the oscillation signal and the quadrature signal and output a quadrature mixed signal, the arctangent demodulation unit is electrically connected to the first mixer and the second mixer and configured to receive the in-phase mixed signal and the quadrature mixed signal and output the demodulated signal to the data acquisition unit.

8. A noncontact vital sign sensing device comprising:
an oscillator configured to output an oscillation signal;
a transmit antenna coupled to the oscillator and configured to receive and transmit the oscillation signal to a subject as a transmitted signal, a reflected signal is configured to be reflected from the subject;
a receive antenna configured to receive the reflected signal as a received signal;
a gain detector coupled to the oscillator and the receive antenna and configured to receive the oscillation signal and the received signal and configured to detect a gain of the oscillation signal relative to the received signal;
a data acquisition unit electrically connected to the gain detector and configured to receive the gain and output a vital sign of the subject according to the gain;
a phase detector, a loop filter and a demodulator, wherein the phase detector is coupled to the oscillator and the receive antenna and configured to detect a phase difference between the oscillation signal and the received signal and output a phase detection signal, the loop filter is electrically connected to the phase detector and configured to receive the phase detection signal and output a feedback signal to a tuning port of the oscillator, the demodulator is coupled to the oscillator and configured to receive the oscillation signal and output a demodulated signal to the data acquisition unit, the data acquisition unit is configured to output the vital sign according the gain and the demodulated signal; and
a first power splitter, a second power splitter and a third power splitter, wherein the first power splitter is electrically connected to the oscillator and configured to receive and split the oscillation signal into three parts, the gain detector, the second power splitter and the demodulator are electrically connected to the first power splitter and configured to receive three parts of the oscillation signal, respectively, the second power splitter is configured to split the received oscillation signal into two parts, the transmit antenna and the phase detector are electrically connected to the second power splitter and configured to receive two parts of the oscillation signal, respectively, the third power splitter is electrically connected to the receive antenna and configured to receive and split the received signal into two parts, the phase detector and the gain detector are electrically connected to the third power splitter and configured to receive two parts of the received signal, respectively.

9. The noncontact vital sign sensing device in accordance with claim 8, wherein the demodulator includes a fourth power splitter, a fifth power splitter, a delay unit, a quadrature power splitter, a first mixer, a second mixer and an arctangent demodulation unit, the fourth power splitter is electrically connected to the first power splitter and configured to receive and split the oscillation signal into two parts, the delay unit is coupled to the oscillator and configured to receive the oscillation signal and output a delayed signal, the quadrature power splitter is electrically connected to the delay unit and configured to receive the delayed signal and output an in-phase signal and a quadrature signal, the first mixer is coupled to the oscillator and the quadrature power splitter and configured to receive the oscillation signal and the in-phase signal and output an in-phase mixed signal, the second mixer is coupled to the oscillator and the quadrature power splitter and configured to receive the oscillation signal and the quadrature signal and output a quadrature mixed signal, the arctangent demodulation unit is electrically connected to the first mixer and the second mixer and configured to receive the in-phase mixed signal and the quadrature mixed signal and output the demodulated signal to the data acquisition unit.

10. A noncontact vital sign sensing device comprising:
an oscillator configured to output an oscillation signal;
a transmit antenna coupled to the oscillator and configured to receive and transmit the oscillation signal to a subject as a transmitted signal, a reflected signal is configured to be reflected from the subject;
a receive antenna configured to receive the reflected signal as a received signal;
a gain detector coupled to the oscillator and the receive antenna and configured to receive the oscillation signal and the received signal and configured to detect a gain of the oscillation signal relative to the received signal;
a data acquisition unit electrically connected to the gain detector and configured to receive the gain and output a vital sign of the subject according to the gain; and
a phase detector, a loop filter and a demodulator, wherein the phase detector is coupled to the oscillator and the receive antenna and configured to detect a phase difference between the oscillation signal and the received signal and output a phase detection signal, the loop filter is electrically connected to the phase detector and configured to receive the phase detection signal and output a feedback signal to a tuning port of the oscillator, the demodulator is coupled to the oscillator and configured to receive the oscillation signal and output a demodulated signal to the data acquisition unit, the data acquisition unit is configured to output the vital sign according the gain and the demodulated signal, wherein the demodulator includes a delay unit, a quadrature power splitter, a first mixer, a second mixer and an arctangent demodulation unit, the delay unit is coupled to the oscillator and configured to receive the oscillation signal and output a delayed signal, the quadrature power splitter is electrically connected to the delay unit and configured to receive the delayed signal and output an in-phase signal and a quadrature signal, the first mixer is coupled to the oscillator and the quadrature power splitter and configured to receive the oscillation signal and the in-phase signal and output an in-phase mixed signal, the second mixer is coupled to the oscillator and the quadrature power splitter and configured to receive the oscillation signal and the quadrature signal and output a quadrature mixed signal, the arctangent demodulation unit is electrically connected to the first mixer and the second mixer and configured to receive the in-phase mixed signal and the quadrature mixed signal and output the demodulated signal to the data acquisition unit.

\* \* \* \* \*